United States Patent
Vincent et al.

(10) Patent No.: US 7,692,189 B2
(45) Date of Patent: Apr. 6, 2010

(54) POLARIZATION-TYPE MOLECULAR COLOR SWITCH

(75) Inventors: Kent D. Vincent, Cupertino, CA (US); Xian-An Zhang, Palo Alto, CA (US); Zhou-Lin Zhou, Palo Alto, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 412 days.

(21) Appl. No.: 11/796,387

(22) Filed: Apr. 26, 2007

(65) Prior Publication Data

US 2008/0266647 A1 Oct. 30, 2008

(51) Int. Cl.
*H01L 51/00* (2006.01)

(52) U.S. Cl. ............ 257/40; 252/586; 257/E51.012; 257/E51.023; 257/E51.026; 349/79; 349/106; 353/84

(58) Field of Classification Search ............... 252/586; 257/40, E51.012, E51.023, E51.026; 349/79, 349/80, 97, 106–109; 353/84
See application file for complete search history.

(56) References Cited

U.S. PATENT DOCUMENTS

| | | | | |
|---|---|---|---|---|
| 6,751,365 | B2 * | 6/2004 | Zhang et al. | 385/2 |
| 7,144,683 | B2 * | 12/2006 | Beck et al. | 430/311 |
| 7,175,961 | B2 * | 2/2007 | Beck et al. | 430/270.1 |
| 7,345,302 | B2 * | 3/2008 | Zhang et al. | 257/40 |
| 7,580,239 | B2 * | 8/2009 | Vincent et al. | 361/311 |
| 2008/0100564 | A1 * | 5/2008 | Vincent et al. | 345/107 |

* cited by examiner

*Primary Examiner*—Anh Phung
*Assistant Examiner*—Michael Lulis

(57) ABSTRACT

A colorant molecule is provided that includes at least one switch unit. The switch unit comprises ring-based tautomers, of which there may be more than one per chromophore, and may include donor and/or acceptor moieties.

22 Claims, 4 Drawing Sheets

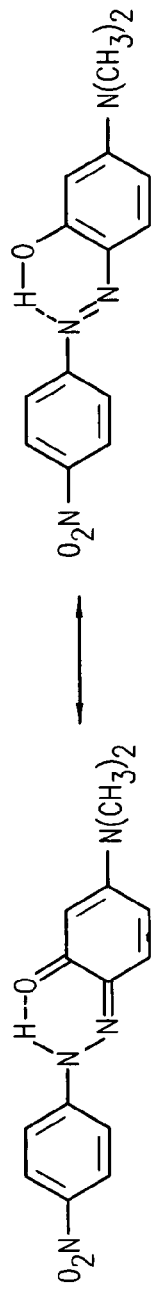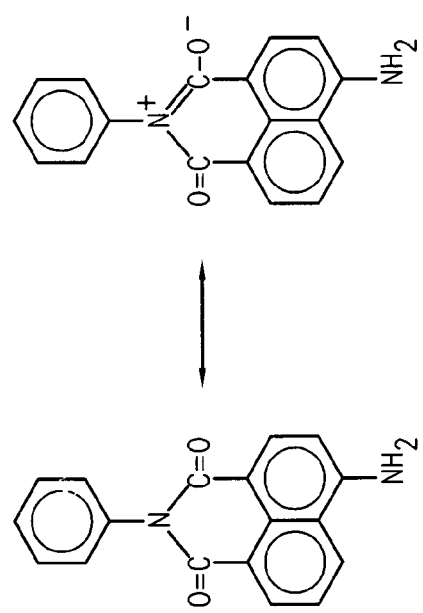
FIG. 1A  FIG. 1B  FIG. 2A  FIG. 2B

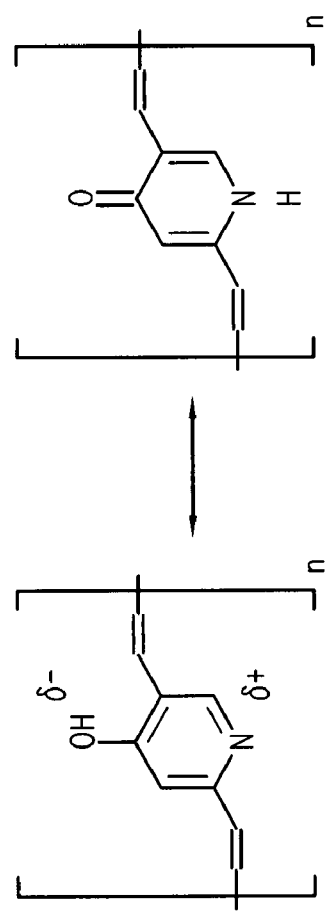
FIG. 3A  FIG. 3B
FIG. 4A  FIG. 4B

POLARIZATION-TYPE MOLECULAR COLOR SWITCH

FIELD

The present disclosure relates to molecular color switches and, more particularly, to molecular color switches activated through a field induced polarization.

BACKGROUND

An important element of the application of the teachings of color switch chemistry is the ability to switch high extinction coefficient chromophores. High extinction coefficient switchable dyes allow thinner colorant films that, in turn, require desirably lower pixel switching voltage for a given electric field in devices such as displays. Chromophores having high extinction coefficients are well known in the dye art and compose commercial dyes used throughout the world. It is, therefore, highly desirable to embody the teachings of intramolecular polarization and tautomerization technology into these commercial chromophores for switching purposes. Following a careful study of commercial chromophore chemistries, it was discovered that many desired switch solutions utilize or require variations of the polarization and tautomer concept not previously disclosed.

Azo chromophores compose roughly half of the commercial dyes used world-wide. In comparison to other commercial chromophores, the azo chromophore uniquely enables high extinction coefficient over a full design range of hue and chroma at relatively low dye cost. For this reason, a color switch design around the azo chromophore is highly desirable. The azo group is normally a bridge group between aromatic rings and is preferably the switching group to break or disrupt $\pi$ electron delocalization between the aromatic rings. This color switching is most easily accomplished by azo tautomerization to a secondary amine. An azo group attached to an aromatic ring has a relatively high electronegativity (0.19) and is, therefore, an electron acceptor that may change polarization and affect the tautomer state when coupled to an electric field. The azo group in a color switch, therefore, may be used as both an acceptor and tautomer, and is located central to the dye molecule, between conjugation units.

Certain dyes, for example those based on the aminonaphthylimide chromophore, have a neutral to charge polarized state tautomer that occurs entirely by intra-molecular charge separation within the tautomer. In some cases, the energy difference between the two tautomer states is sufficiently small that the tautomer reversibly and continuously switches between tautomer states at room temperature. In the case of the aminonaphthylimide chromophore, the charged state forms a $\pi$ conjugation link between two aromatic groups while the uncharged state breaks the conjugation link. In this instance, both the acceptor and donor comprise the tautomer group.

Many dye structures are large in nature, include multiple chromophore units (e.g., disazo, trisazo) and auxochromes. Such large structures, or even small structures, can require transformation energies greater than can be coupled into the molecule through a single acceptor-donor and an electric field of desired intensity and below the dielectric strength of the material set. Further, dye chromophores often exhibit dichroism, wherein the extinction coefficient of the dye varies depending on the orientation of the molecule with the observed optical axis. Typically, the extinction coefficient diminishes as the length-wise axis of the colorant molecule aligns with the optical axis. Dye structures are known wherein the acceptor-donor induced dipole of the colorant molecule aligns with the length-wise axis of the molecule, which in turn is aligned with both the electric field and optical axis. In some instances, this orientation produces maximal extinction coefficient loss due to dichroism. For such cases, it is highly desirable to align the acceptor-donor axis orthogonal to the length-wise axis of the colorant molecule. Such an orientation, however, effectively prohibits a single electron acceptor-donor pair from effecting conjugation along the entire length of the colorant molecule. It is thereby desirable in such cases to include multiple acceptor-donor pairs within a given colorant molecule to improve field energy coupling, dichroism or both. Molecular designs have been taught wherein a single electron-accepting group and a single donor group are structured with at least one tautomerizable atomic group and at least one conjugating fragment. Still further, the use of multiple acceptor-donor/tautomer groups along a molecule is desirable for polymeric switchable colorants and colorants having more than two color states. Polymeric color switches promise the ability to switch between very highly conjugated color states, such as black, and very narrowly conjugated color states, such as found in transparent molecules. Polymeric color switches also offer colorant films in which the switchable colorant and holding polymer matrix are one and the same and thereby potentially improve color density per film thickness. Colorants having more than two switchable color states promise, for example, the ability to separately display each of a set of trichromatic colors in a single pixel.

Certain tautomers undergo a change in conformation from one tautomer state to another. Such conformation change can create steric hindrance or proton transfer distances that interfere with reversible switching. It is therefore desirable to select tautomer groups that maintain conformation and small proton transfer distances between tautomer states. Tautomers contained within a ring or an open ring can provide these properties. For example, a cyclic amine-imine tautomer maintains conformation and an approximately one angstrom (Å) proton transfer distance when tautomerizing from the amine to imine form.

SUMMARY

In accordance with an embodiment of the invention, a colorant molecule is provided that includes at least one switch unit, based on tautomerization. The switch unit may include any combination of acceptor/donor groups and tautomer groups.

BRIEF DESCRIPTION OF THE DRAWINGS

FIGS. 1A-1B illustrate an example of an azo dye color switch wherein the bridging azo group functions both as an acceptor and as a tautomer, in accordance with an embodiment.

FIGS. 2A-2B illustrate an example of an aminonaphthylimide dye having a carbonyl-amine acceptor-donor pair that reversibly tautomerizes at room temperature, in accordance with an embodiment.

FIGS. 3A-3B illustrate an example of a color switchable polymer, in accordance with an embodiment.

FIGS. 4A-4B illustrate an example of a switchable molecule incorporating an open ring tautomer, in accordance with an embodiment.

DETAILED DESCRIPTION

Figure 5A:
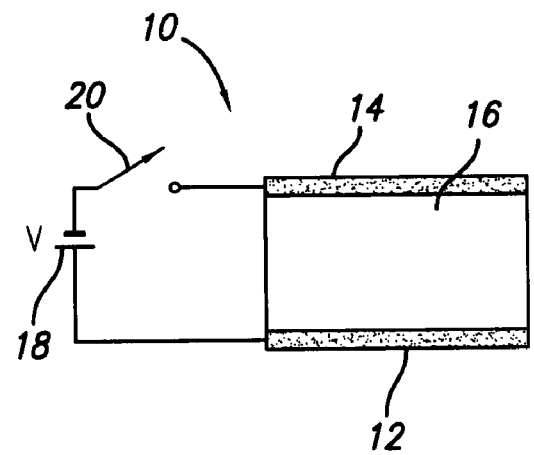
FIGS. 5A-5B depict embodiments of a simple switch, employing the switchable molecules of the invention.

As used herein, the term "tautomerization" refers to a tautomer that may convert between two neutral states or between neutral and charge separated states.

The commercial dye art includes a large number of chromophores that exhibit high extinction coefficient. These are generally classed by the Society of Dyers and Colourists (Great Britain) and the American Association of Textile Chemists and Colorists and include but are not limited to: nitroso, nitro, monoazo, disazo, trisazo, polyazo, azoic, stilbene, carotenoid, diphenylmethane, triarylmethane, xanthene, acridine, quinoline, methine, polymethine, thiazole, indamine, indophenol, azine, oxazine, thiazine, sulfur, lactone, aminoketone, hydroxyketone, anthraquinone, indigoid, phthalocyanine, natural organic, oxidation base, and inorganic chromophores. Dye chromophores generally comprise aromatic groups interconnected by a bridging group or groups that provide a π electron conjugation link between the aromatic groups. Such bridging groups include, for example, azo, vinylene, methylene, cyclic methylene, cyclic bisketone, imine, dihydropyrazine, dihydrooxazine, cyclohexanedione, cyclic amide, and cyclic ketone links. A copending patent application Ser. No. 10/945,756, filed Sep. 21, 2004 (U.S. Publication No. 2006/0060836 A1, published on Mar. 23, 2006) and incorporated herein by reference, discloses the bridging group including or adapted to include a tautomer for switch purposes, since the bridge serves as a natural conjugation switch point for the chromophore. For some bridging groups, for example, azo and cyclic amides, the acceptor and/or donor and tautomer may be coincidental. For some bridging groups, such as cyclic amides, the tautomer changes between neutral and charge separated states. Examples of each of these bridging groups follow.

In accordance with an aspect of the present invention, a switchable molecule having at least one switch unit is disclosed. The at least one switch unit includes an acceptor moiety, a donor moiety, and a tautomer group, with tautomerization occurring within a ring that remains substantially conformationally unchanged. The molecule is colored in at least one of the two states. By "substantially conformationally unchanged" is meant that a small change in conformation, e.g., on the order of 5 to 10 degrees may likely not affect the performance of devices employing the switchable molecule.

FIGS. 1A-1B depict an example of an open ring tautomer within a molecule. As can be seen, the tautomerization depends on a proton reversibly moving between the diazo nitrogen atom (FIG. 1B) and the quinine oxygen atom (FIG. 1A). It will be noted that the proton moves back and forth along the hydrogen bond between the nitrogen and oxygen atoms, a distance of about 1 Å. The molecule has conjugation that changes from the non-conjugated state (hydrazo form) to the conjugated state (azo form), wherein the molecule evidences a different color in each state. Thus, there is a change in the extended conjugation as a consequence of the tautomerization.

The aminonaphthylimide dye (6-amino-benzo[de]isoquinoline-1,3-dione) shown in FIG. 2A has a carbonyl-amine acceptor-donor pair that reversibly tautomerizes at room temperature to the charge separated form shown in FIG. 2B. The room temperature tautomer reversibility occurs because the energy difference between the two tautomer states (as computed by AM1 molecular models) falls below kT at room temperature. The cyclic amide of FIG. 2A forms an unconjugated bridge that localizes the π electrons to the adjacent aromatic rings.

In the charge-separated form of FIG. 2B, the cyclic amide forms a conjugated bridge that promotes π electron delocalization between the adjacent aromatic rings (spectrally red shifted state). The rapid equilibrium cycling between the neutral and charge separated states allows the aminonaphthylimide dye to be visually perceived as colored as if in a stable charge separated state of FIG. 2B.

In accordance with the present teachings, the charge-separated state may be prevented by application of an electric field having a polarity across the dye molecule that opposes charge separation. With electric field activation, the aminonaphthylimide dye remains in the blue shifted spectral state of FIG. 2A. The aminonaphthylimide is thus color switched between charge separation/recombination equilibrium and charge neutral tautomer states.

The molecule shown in FIGS. 2A-2B (6-amino-benzo[de]isoquinoline-1,3-dione) has a resonance structure. The electronic structure only is changed, not the physical structure, through charge separation. The neutral form (FIG. 2A) is colorless, while the charged state (FIG. 2B) is yellow.

FIGS. 3A-3B show an example of a color switchable polymer in accordance with an embodiment. In one embodiment, the value of n may be in the range of 2 to 7000. It is well known that, in general, the spectral absorption of a colorant shifts to longer wavelengths with broader and more absorptive peaks (higher extinction coefficient) as the extent of conjugation increases. Extended conjugation along a fully conjugated polymer, therefore, provides an attractive switch option. In the present example, the monomeric repeat unit comprises a fully conjugated enol-pyridine chromophore that tautomerizes under electric field to a non-conjugated, transparent keto-piperidine form. Although not necessary to the present teachings, the acceptor-donor pair and tautomer groups in this example are one and the same. The intervening alkene groups form a conjugation bridge between each repeated chromophore along the polymer backbone and allow full conjugation along the polymer in its repeated pyridine form, rendering the polymer colored. Upon field polarization, the extended conjugation across the polymer is transformed to localized π electron conjugation within each keto-piperidine repeat unit, promoting a polymer transparent state. One skilled in the art will recognize that a variety of bridging groups, chromophores, acceptor-donor pairs, and tautomers may be employed within the general teachings of this invention. Bridging units, for example, include, but are not limited to, alkenes, alkynes and azo groups.

The molecule shown in FIGS. 3A-3B also has a resonance structure, which can be stabilized by the application of an external electric field (not shown). The quinone tautomer form (FIG. 3B) is colorless, while the phenol tautomer form (FIG. 3A) is yellow for short polymer chains (e.g., n=10), with increasing blue color shift and extinction coefficient as the polymer chain is increased in size (e.g., n>10).

FIGS. 4A-4B depict another example of an open ring tautomer within a molecule, similar to FIGS. 1A-1B. As can be seen, the tautomerization depends on a proton reversibly moving between the aniline nitrogen atom (FIG. 4B) and the quinine oxygen atom (FIG. 4A). It will be noted that the proton moves back and forth along the hydrogen bond between the nitrogen and oxygen atoms, a distance of about 1 Å. As seen in this molecule, the molecule has conjugation that changes from the non-conjugated state (amine form; FIG. 4A), yellow color, to the conjugated state (imine form; FIG.

4B), transparent. Thus, there is a change in the extended conjugation as a consequence of the tautomerization.

The formation of a six-membered ring is depicted in FIGS. 1A-1B and 4A-4B. However, it will be immediately apparent to one skilled in the art that five- and seven-membered rings may be formed by the same process, employing the teachings set forth herein.

In all four cases of the molecules depicted above, tautomerization is occurring within a ring. The ring does not conformationally change; rather, electron ($e^-$) or proton ($H^+$) exchange occurs within the ring. The ring remains in the same plane and the atomic distances remain the same throughout the tautomerization.

As is well known in the organic chemistry art, there are many combinations of electron acceptor and donor moieties that may be paired and used within the teachings of the present invention. As each acceptor and donor group has a different electronegativity, the many possible acceptor-donor pairs each offer a different and, generally, unique dipole moment. In the present teachings, chromophores are bridged, wherein each chromophore and/or bridge has an incorporated acceptor-donor and tautomer (which may be one and the same or not). It is, therefore, possible within these teachings to bridge chromophores that incorporate, by design, acceptor-donor dipole moments different from their adjoining chromophores. It is further noted that the tautomer switching energies within each chromophoric element also typically vary according to the chemistry of the chromophore, its bridge coupling, tautomer, acceptor-donor pair, and other of its chemical components. The combination of different dipoles and switching energies may, therefore, be used to allow each chromophoric element within a colorant to switch on and off at a different electric field intensity from adjoining chromophoric elements. Thus, the extent of π electron conjugation across the colorant, and hence the color at a given π electron delocalization state, may be controlled through field intensity to include multiple (more than two) color states. In this case, in addition to a full field ON color state and field OFF color state, there are intermediate color states (colors) that switch on or off as the field is raised between the full field intensity on and off conditions.

In some embodiments, the switchable molecule may be situated in a medium, such as a liquid or solid medium. Close range electric fields induced between medium and molecule dipoles polarize the molecule in a manner similar to that induced through an external field. The close range electric fields are generally more intense and, depending on dipole strengths, are independently capable of switching the color of the molecule. A molecule dissolved in a polar solvent, for example, can be switched by solvent-molecule dipole-dipole interaction to a second tautomer state and then switched back to its first tautomer state through solvent exchange with a less polar solvent. A molecule of the type shown in FIGS. 4A-4B, for example, is switched to a yellow color state when dissolved in a polar solvent, such as anisole, but is switched back to a colorless state when exchanged into a non-polar solvent such as toluene.

In one embodiment, the medium is selected so that the medium-molecule dipole-dipole interaction pre-polarizes the molecule to a near switch state. The external field is then added to invoke switching. In another embodiment, the molecule is dissolved in a bulk polarizable medium such as a liquid crystal. The external field, in this instance, is used to change the orientation of the liquid crystal, for example from a disordered (field OFF) to ordered (field ON) state. The change in order affects the medium-molecule dipole-dipole interaction in a manner that induces a change in the switch state of the molecule. In this instance, the external electric field indirectly switches the molecule by affecting the dipole orientation of the medium. The type of liquid crystal (e.g., nematic, smectic, chiral, ferroelectric) selected to best invoke molecule switch function is dependent on the structure and dipole moments of both the molecule and liquid crystal, as each affects the dipole-dipole spacing and interaction. The use of a bulk polarizable medium helps to overcome the affect of thermally-induced motion that normally opposes switching.

Acceptor and donor moieties may be included in the molecule and, indeed, one or the other or both may be part of the tautomer. Acceptor moieties are usually defined as moieties that are electron-withdrawing; non-limiting examples include hydrogen; hetero atoms including at least one of N, O, S, P, F, Cl, and Br; functional groups containing at least one of these hetero atoms; saturated hydrocarbons; unsaturated hydrocarbons; substituted hydrocarbons; carboxylic acids, carboxylic esters, amides, nitro groups; nitrites; carbonyls; cyano groups; azo groups; sulfuric acids; sulfuric esters; sulfuric amides; phosphoric acids; phosphoric esters; phosphoric amides; and mixtures thereof. Donor moieties are usually defined as moieties that have unbonded electrons; non-limiting examples include functional groups containing at least one hetero atom including at least one of B, Si, I, N, O, S, and P; hydrogen; amines; OH; SH; ethers; saturated hydrocarbons; unsaturated hydrocarbons; substituted hydrocarbons; and mixtures thereof, with the proviso that the donor is more electropositive than the acceptor.

Any of the molecules depicted herein include acceptor and donor moieties, which provide polarization in the molecule. The acceptor and donor groups provide a mechanism for electric field energy coupling into the molecule, from both the external field and medium. For example, in FIGS. 1A-1B, the acceptor group is the nitrophenyl ring, while the donor group is the N, N-di methyl aniline, attached to the nitrophenyl ring with a diazo group. The donor group is the tautomerizable portion of the molecule. In FIGS. 2A-2B, the acceptor group is the phenyl ring attached to the imide nitrogen atom, while the donor group is the amine attached to the fused ring. The tautomerization mainly occurs at the imide group. In one of the tautomers, π-electron delocalization is established between the acceptor and the donor (FIG. 2B), while in the other tautomer, the π-connection is disrupted between the acceptor and the donor (FIG. 2A). In FIGS. 3A-3B, the acceptor is the nitrogen heteroatom in the ring, while the donor is the OH attached to the ring. The tautomer includes both the donor and the acceptor. In FIGS. 4A-4B, the acceptor is the nitro group attached to the left ring, while the donor is the N, N-dimethyl amino group attached to the right ring. One of the tautomer structures of the molecule disrupts the π-delocalization between the donor and acceptor (FIG. 4A), and the other tautomer structure restores the π-delocalization (FIG. 4B).

Summarizing, the colorant molecule may include more than one switch unit per colorant molecule, such as the polymer of FIGS. 3A-3B. A switch unit includes any combination of acceptor-donor and tautomer groups, wherein the acceptor-donor pair contributes energy, either naturally or through coupling with an electric field, as necessary to invoke tautomerization that localizes or delocalizes associated π electrons. The acceptor and/or donor group may be incorporated as part of a tautomer group. That is, the acceptor and/or donor may tautomerize.

A multi-color polarization-type colorant molecule may have multiple acceptor-donor pairs, of which certain pairs have a different polarization strength than others. The different polarizations allow selective switching along the colorant molecule such that the extent of π electron delocalization may be controlled between more than two color states with increasing electric field strength. For example, referring to the polymer of FIGS. 3A-3B, different segments may have different acceptor/donor groups. A low voltage may switch a first segment but no others, thereby providing, e.g., yellow. A higher voltage may switch the first and a second segment, thereby shifting the absorption further toward blue, and so forth. In this instance, the polymer may most likely be a condensation polymer to allow such segmentation.

The molecules disclosed herein only need to have one switch unit. However, it may be advantageous to include more than one switch unit to better control the extent of π electron localization for transparency and to couple more switching energy into the molecule.

Each switch unit in a molecule comprises at least one acceptor/donor and at least one tautomer, but the acceptor and/or donor may be part of the tautomer or separate.

Other examples of molecules involving the molecules depicted in FIGS. 1A-1B and 4A-4B may include replacing the nitro group and or the amine group. For example, a methyl ester may be substituted for the nitro group in FIGS. 4A-4B, resulting in a molecule that switches from transparent (imine form) to yellow (amine form). In this connection, the molecule depicted in FIGS. 4A-4B may be preferred in some embodiments, as the switch state conversion in a solvent exchange has been found to be virtually 100%.

Figure 5B:
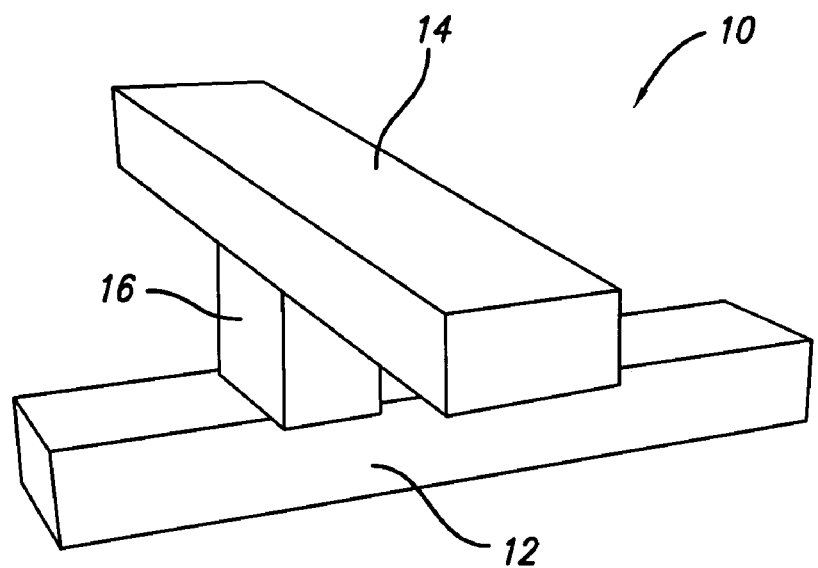

The switchable molecules described herein are useful in a variety of switching devices, such as electrical and optical switches, displays and other such devices. FIG. 5A-5B depict a simple switch 10 comprising a bottom electrode 12 and a top electrode 14. In one embodiment, the switch 10 may be in the configuration of two parallel capacitor plates 12, 14, as shown in FIG. 5A. The switchable molecule 16 is situated between the two plates 12, 14. In another embodiment, the switch 10 may be in the configuration of two crossed wires 12, 14, one wire crossing the other at a non-zero angle, thereby forming a junction, as shown in FIG. 5B. The switchable molecule 16 is situated in the junction between the two wires 12, 14. The switchable molecule may be pre-oriented through electric field poling as the incorporating medium is solidified. Alternately, the switchable molecule may be dissolved in liquid or a liquid crystal, as disclosed above.

Figure 5C:
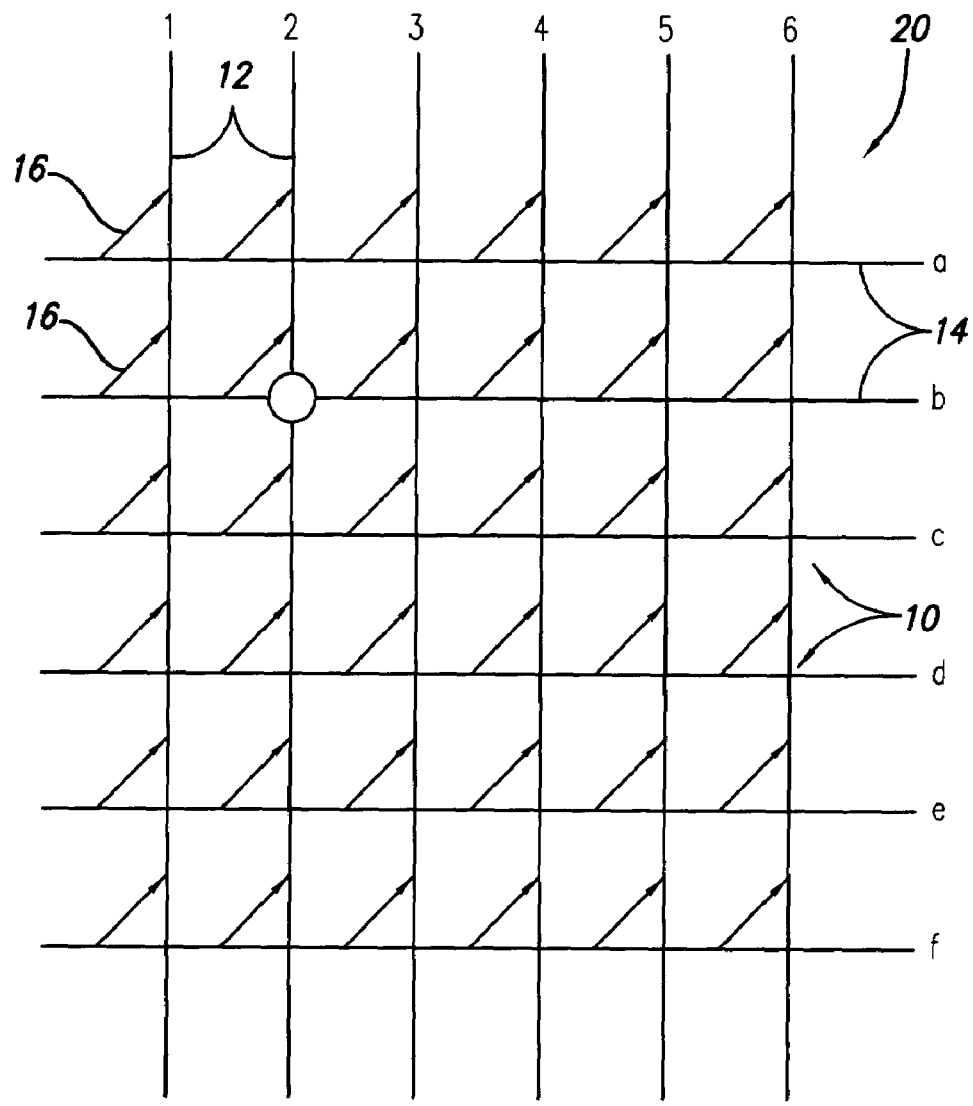
FIG. 5C is a schematic representation of a two-dimensional array of switches, depicting a 6×6 crossbar switch.

The switch 10 may be a single switch, as shown, or an array of switches. FIG. 5C depicts a two-dimensional array 20 of switches 10, which forms a crossbar. Specifically, a 6×6 array 20 is depicted. However, it is to be understood that the embodiments herein are not to be limited to the particular number of elements, or switches 10, in the array 20. Access to a single point, e.g., 2b, is done by impressing voltage on wires 2 and b to cause a change in the state of the molecule 16 at the junction thereof, as described above.

Embodiments of the present disclosure offer many advantages, including, but not limited to, the following. Embodiments of the switchable molecules may be used as a switching mechanism in electronic and/or optical devices. The molecules are advantageously reversibly switchable between two different energetic states, a conjugated-connected state and a conjugated-disconnected state, when exposed to an electric field, electromagnetic field, reversed electric field, or a reversed electromagnetic field. Further, embodiments of the switchable molecule are neither oxidized nor reduced, which substantially advantageously avoids breaking of chemical bonds and potentially initiating an irreversible reaction. Still further, embodiments of the switchable molecule undergo a minimal physical change in switching between the connected and disconnected states, and as a result, the switching time may be reduced.

What is claimed is:

1. A switchable molecule having at least one switch unit, the at least one switch unit including an acceptor moiety, a donor moiety, and a tautomer group, with tautomerization occurring within a ring, with the molecule remaining substantially conformationally unchanged, the molecule being colored in at least one of two or more states.

2. The switchable molecule of claim 1 situated in either a liquid or solid medium.

3. The switchable molecule of claim 2 situated in a liquid crystal medium.

4. The switchable molecule of claim 1 wherein the ring comprises 5 to 7 members, each member selected from the group consisting of carbon, nitrogen, and oxygen atoms.

5. The switchable molecule of claim 4 wherein the ring comprises 6 members.

6. The switchable molecule of claim 1 wherein the tautomerization occurs with a ring that includes a hydrogen bond, wherein the position of the hydrogen bond in the ring changes from a first state to a second state.

7. The switchable molecule of claim 6 having the diazo structure shown in FIGS. 1A-1B.

8. The switchable molecule of claim 7 having the structure shown in FIGS. 4A-4B.

9. The switchable molecule of claim 1 having the resonance structure shown in FIGS. 2A-2B.

10. The switchable molecule of claim 1 having the resonance structure shown in FIGS. 3A-3B.

11. A molecular switching device, comprising: at least one bottom electrode; at least one top electrode; a switchable molecule situated between the at least one bottom electrode and the at least one top electrode, the switchable molecule having at least one switch unit, the at least one switch unit including an acceptor moiety, a donor moiety, and a tautomer group, with tautomerization occurring within a ring, with the molecule remaining substantially conformationally unchanged, the molecule being colored in at least one of at least two states.

12. The molecular switching device of claim 11 situated in either a liquid or solid medium.

13. The molecular switching device of claim 12 situated in a liquid crystal medium.

14. The molecular switching device of claim 11 wherein the ring comprises 5 to 7 members, each member selected from the group consisting of carbon, nitrogen, and oxygen atoms.

15. The molecular switching device of claim 14 wherein the ring comprises 6 members.

16. The molecular switching device of claim 11 wherein the tautomerization occurs with ring closing to a first state and ring opening to a second state occurring through hydrogen bonding.

17. The molecular switching device of claim 16 having the diazo structure shown in FIGS. 1A-1B.

18. The molecular switching device of claim 16 having the structure shown in FIGS. 4A-4B.

19. The molecular switching device of claim 11 having the resonance structure shown in FIGS. 2A-2B.

20. The molecular switching device of claim 11 having the resonance structure shown in FIGS. 3A-3B.

21. The molecular switching device of claim 11 having a capacitor configuration, with the at least one bottom electrode and the at least one top electrode comprising two parallel plates and the switchable molecule situated therebetween.

22. The molecular switching device of claim 11 having a crossed electrode configuration, with one electrode crossing the other at a non-zero angle, thereby forming a junction, and with the switchable molecule situated in the junction.

* * * * *